United States Patent [19]

Kortright et al.

[11] Patent Number: 5,059,518

[45] Date of Patent: Oct. 22, 1991

[54] STABILIZED LYOPHILIZED MAMMALIAN CELLS AND METHOD OF MAKING SAME

[75] Inventors: Kenneth H. Kortright, Davie; Robert H. Raynor, Miramar; Stephen F. Healy, Jr., Miami, all of Fla.

[73] Assignee: Coulter Corporation, Hialeah, Fla.

[21] Appl. No.: 260,260

[22] Filed: Oct. 20, 1988

[51] Int. Cl.$^5$ .......................... A01N 1/02; C12Q 1/68; G01N 33/569

[52] U.S. Cl. ........................................... 435/6; 435/1; 435/2; 435/7.21; 435/7.23; 435/7.24; 435/29; 435/34; 435/240.2; 435/240.27; 435/243; 435/260; 436/8; 436/10; 436/63; 436/64

[58] Field of Search .................... 435/1, 2, 6, 7, 29, 435/34, 240.2, 243, 260, 240.27; 436/8, 10, 63, 64

[56] References Cited

U.S. PATENT DOCUMENTS

| | | | |
|---|---|---|---|
| 4,649,106 | 3/1987 | Schlossman et al. | 435/34 |
| 4,874,690 | 10/1989 | Goodrich, Jr. et al. | 435/2 |

FOREIGN PATENT DOCUMENTS

| | | |
|---|---|---|
| 8705300 | 9/1987 | Int'l Pat. Institute . |
| 0012317 | 2/1981 | Japan . |
| 0007419 | 1/1982 | Japan . |
| 0131913 | 8/1983 | Japan . |
| 2187191 | 9/1987 | United Kingdom . |
| 8700196 | 1/1987 | World Int. Prop. O. . |

OTHER PUBLICATIONS

Moran et al., *Science*, 198, 149-157, 1977.

*Primary Examiner*—David A. Saunders
*Attorney, Agent, or Firm*—Myron C. Cass

[57] ABSTRACT

A method of lyophilizing mammalian cells to produce preserved human cells, hybridoma cell lines, tissue cells, and control cells for immunoassays and other hematological measurements. Prior to freezing and lyophilizing, the prepared mammalian cell pellet is suspended in a solution of trehalose in an isotonic fluid prepared at a specified optimal concentration and incubated at room temperature for a designated time period. The lyophilized cells when rehydrated, retain their optimal physiological characteristics suitable for use as an analytical control and retain said characteristics after storage at 2°–8° C. for a period in excess of five (5) months.

20 Claims, 5 Drawing Sheets

---

LYOPHILIZATION PROCEDURE FOR CELLS

CULTURED CELLS OR PERIPHERAL BLOOD LYMPHOCYTES SUSPENDED IN 1% PHOSPHATE BUFFERED ALBUMIN.

↓

CELLS PELLETED BY CENTRIFUGATION.

↓

CELL PELLET RESUSPENDED IN 10% TREHALOSE (ISOTONIC SOLUTION).

↓

CELLS PELLETED BY CENTRIFUGATION.

↓

CELL PELLET RESUSPENDED IN 10% TREHALOSE (ISOTONIC SOLUTION).

↓

CELL SUSPENSION VIALED AT 300 μL SOLUTION/VIAL

↓

VIALS CHILLED TO 4°C.

↓

VIALS PLACED IN -70°C FREEZER FOR 1 HOUR.

↓

VIALS PLACED IMMEDIATELY IN LYOPHILIZER (15 HOUR CYCLE).

↓

STORED AT 4°C

PROCEDURE APPLICABLE TO CELL LINES OR PBLS

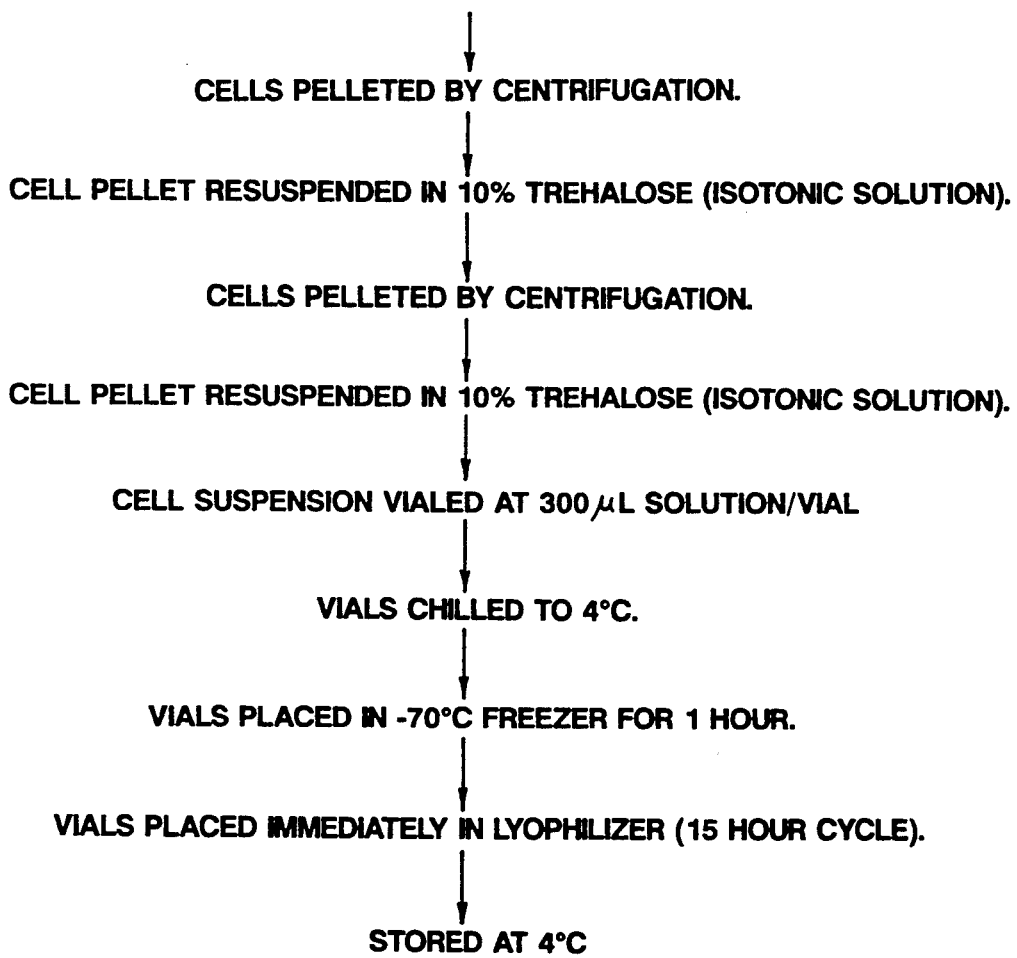

5,059,518

STABILIZED LYOPHILIZED MAMMALIAN CELLS AND METHOD OF MAKING SAME

FIELD OF INVENTION

This invention relates generally to the technology of lyophilizing biological materials and more particularly, relates to a novel method of lyophilizing mammalian cells to produce preserved human cells, hybridoma cell lines, tissue cells and control cells for immunoassays and other hematological measurements, all having stability and shelf life characteristics heretofore never realized and with substantially equivalent physiological parameters as compared to fresh cells.

BACKGROUND OF THE INVENTION

Methods of lyophilization or freeze drying for preserving liposomes containing biologically active molecules and for bacterial cultures are known. Preparation of pharmaceutical tablets using lyophilizing procedures also are known. In U.S. Pat. No. 4,678,812, a method preparing tablets useful in diagnostic applications utilizing trehalose as an excipient and stabilizer is disclosed. U.S. Pat. No. 4,712,310 teaches a method of preparing tablets useful as reagent carriers for diagnostic assays.

Methods of encapsulating materials such as drugs, nucleic acids, proteins, reporter molecules, enzymes and the like into liposomes are taught in prior art patents. Examples of such patents are U.S. Pat. Nos. 4,515,736 and 4,411,894. U.S. Pat. Nos. 3,261,761, 4,206,200 and 4,246,349 teach lyophilizing procedures for bacteria. In this same study area is the published European Patent Application No. 0 259 739, published Mar. 16, 1988, entitled "Improved Stability of freeze-dried cultures".

The prior art identified addresses the technique of using sugars in their lyophilization applications for a stabilizing function. The sugar trehalose also is mentioned as being useful for this function. In International Application published under the PCT, No. WO 86/03938 published July 17, 1986, there is disclosed use of trehalose as a preserving agent, both inside the liposomes and externally, in solution, during freeze-drying. This use of trehalose both externally and internally of liposomes is the preferred embodiment noted.

None of the prior art technology described undertakes to preserve mammalian cells and particularly human cells. Human cells such as blood cells are distinctive in their membrane structure as compared to the membrane structure of bacteria or liposomes. In the case of bacteria, the cell wall is a very thick non-lipid wall whose function is to protect the cell fluid contents from such adverse effects as heat, osmotic pressure changes and even freeze-drying in the absence of a preserving agent, such as a sugar. Thus, many strains of bacteria can withstand the stresses of freezing and drying in the absence of a unique preserving protective or coating because of their rigid cell wall.

In the case of liposomes, the fluid space is enclosed by unilamellar or multilamellar lipid vesicles. The walls of the vesicles are formed by a biomolecular layer of one or more lipid components having polar heads and non-polar tails. In an aqueous solution, the polar heads of one layer orient outwardly to extend into the surrounding medium, and the non-polar tail portions of the lipids associate with each other, thus providing a polar surface and a non-polar core in the wall of the vesicle. Unilamellar liposomes have one biomolecular layer whereas multilamellar liposomes generally have a plurality of substantially concentric biomolecular layers. Thus, the liposome is a spherical microstructure formed when mixtures of phospholipids with or without steroids are dispersed in aqueous solutions. They are envisioned as useful for encapsulating an agent for recognized delivery to an in vivo site.

The liposome cell wall is an artificial bi-lipid membrane as compared to that of a human cell, for instance. The composition of a human cell membrane is much more complex. In addition to a bi-lipid membrane structure, the human cell membrane has many additional protein and glycoprotein molecules intercolated into its lipid bi-layer. These proteinaceous molecules are of particular interest in that they provide cell surface antigens or determinant sites not present in an artificial liposome. The investigation of human cell surface markers is the crux of immunoassays and other hematological measurements relating to human blood cells. The same distinction over liposomes is apparent in use of hybridoma cell lines and monoclonal antibodies. Another distinction to keep in mind is the difference between the complex fluid contents of a mammalian cell and that of a liposome, for instance. In the instance of a human blood cell, the cell exists only in an isotonic fluid medium which is not the case for liposome which may exist in any medium, including non-isotonic solutions.

The lyophilizing method embodying the invention is unique in that mammalian cells are lyophilized without adversely changing the morphology of the cell and without rendering the cell membrane permeable after conjugation to a probe or marker for its application in an assay, for instance, when constituted as a control cell. Further, said lyophilizing method functions to stabilize the proteinacious structure of the cell membrane and its orientation within the cell wall so that the membrane surface protein markers are not destroyed. Considering the known fragile character of the cell membrane of mammalian cells, the results achieved by the lyophilization method of the herein invention are believed to have been unexpected and suprisingly effective in terms of stability and shelf life of the lyophilized mammalian cell achieved as well as retaining physiological functional characteristics after rehydration as compared to fresh cells.

In practicing the method embodying the invention, the sugar trehalose in an isotonic solution is utilized as a preservative or protective coating on the exterior surface only of a mammalian cell. Coating the interior surface of the cell membrane would not be feasible. The characteristics of excellent stability and longevity of shelf life achieved enables the invention to be applied to producing control cells for immunological assays, for use in assuring proper sample preparation for flow cytometric analyses of mammalian cells, for blood cell counting, sizing and analysis of subsets of blood cell constituents, such as red cells and white cells and in DNA analysis for a variety of cell types. Thus, various types of cells can be lyophilized and thereafter reconstituted for successful biological cell analysis.

In Stefi Weisburd, "Death Defying Dehydration", Science News, Vol. 133, No. 7, pp. 97–112, Feb. 13, 1988, there is described a process for freeze-drying liposomes using trehalose as described in said International Application under PCT No. WO86/03938. The publication described research conducted with microorganisms and showing that trehalose, a low molecular weight sugar, was produced in high concentrations in these micro-organisms as they dehydrated. It was considered that trehalose acted as a lipid stabilizer to increase the stability of the artificial cell-membranes or liposomes. The publication cautions that trehalose may not be a useful additive in all situations and that the toxicology of trehalose should be noted.

The need for accurate and reliable control media which can be assayed concurrently with the test samples to realize proper sample preparatory technique and laboratory test instrument function is a continuing one. In flow cytometric analysis, no established controls are available except fluorescent beads or microspheres which are used to set the flow cytometer operating parameters. The most desirable control substance would be one that could control for reagents utilized and sample preparatory technique along with proper instrument function. Thus, for flow cytometric analyses, preserved mammalian cells expressing the required antigenic determinant or determinants to be assayed along with cells of the test sample would present an optimal control medium. Previously determined values for the control cells could be compared with test results obtained by the researcher.

The nature of flow cytometric analysis for all surface antigens requires a preparatory method for the control cells which preserves cellular light scattering patterns and membrane integrity with minimal damage to the cell surface antigens being studied. The best basis of comparison for these factors would be fresh cells having the known properties to be studied. However, shipment and storage of fresh control cells in a laboratory environment would be impractical from a commercial supply standpoint.

Thus, preserved mammalian cells such as by lyophilization which could be shipped and stored for a desirable shelf life period and reconstituted or rehydrated at the time of use while retaining the necessary characteristics for its use would provide a desirable control for flow cytometric analyses.

Such lyophilized mammalian control cells also would be suitable for use with hematology analysis instruments, such as the COULTER COUNTER® blood cell analyzer marketed by Coulter Electronics, Inc. of Hialeah, Fla., a wholly owned subsidiary of Coulter Corporation, assignee of record.

Applicants believe that freeze-drying of mammalian cells for use as control media has not been successfully achieved for several reasons. For instance, the freezing parameters adversely affects proteinacious molecules in such cells and can destroy all membrane integrity.

Experimental work utilizing a variety of sugars in combination with DMSO or glycerol to counter the adverse effects of intra-cellular freezing were undertaken. Also, sugars alone were utilized in the lyophilizing procedure wherein the sugar was added to the lyophilization carrier solution, such as standard normal goat serum, for the cells in suspension during the freeze down and lyophilization procedure employed. Various dilutions of sugars with and without DMSO, phosphate buffered albumin (PBA), fetal calf serum, Human AB Serum and Normal Goat Serum were tried.

Experiments using sucrose, taurine and glucose, and DMSO with sugar as a carrier all were unacceptable in results achieved. For example, incidents of decrease in specific fluorescence for some antigens relative to fresh cells, unacceptable light scatter and specific fluorescence characteristics were determined when fructose was used. The treatment of cells using such sugars still provided unsatisfactory lyophilized cells such that the cells were not properly prepared to prevent major damage during freeze down. Such damage was expressed in molecular change in cell membrane proteins, such as conformation alterations which could affect antigen expression. Cryoprotectorants are needed to routinely prevent such damage that occurs as a result of increased salt concentrations and crystal formation during freezing of cells. Such cryoprotectorants as DMSO and glycerol, as well as other serums, were found to be unsuccessful for lyophilization of mammalian cells by applicants.

The use of normal goat serum as a matrix or carrier in which the cells are suspended during freeze-down and lyophilization did not provide optimal cell surface marker survival. It was believed that the protein in the serum did not protect the cell membrane from oxidation and other disruption. Trehalose used only and in mixtures with normal goat serum and albumin also proved to be unsuccessful in solving the problems alluded to herein.

Thereafter, experiments were conducted using the sugar trehalose as part of several carrier formulas including mixtures with normal goat serum and albumin without achieving an acceptable lyophilized control cell medium. Thus, the use of sugars, including trehalose for stabilizing membrane lipids of cells during lyophilization proved unsuccessful.

The method embodying the invention which proved successful for providing acceptable lyophilized mammalian cells comprises utilizing the sugar trehalose in an isotonic solution for preparing the cells for the rigor of the freeze-down and lyophilizing protocols. The lyophilized control cells produced by the inventive method included hybridomas or cell lines and peripheral blood mononuclear cells which retained optimal characteristics for use in flow cytometer analyses. An optimal trehalose concentration in isotonic solution also was determined with trehalose being the most acceptable sugar for use in the inventive method. The invention includes the lyophilized mammalian control cells and other human cells capable of being produced by said lyophilization method.

SUMMARY OF THE INVENTION

The method of producing lyophilized mammalian cells for use as a biological control in immunoassays, flow cytometric analyses and microscopic assays and for preserving human cell lines which have retained their desired antigenicity. The lyophilized cells can be reconstituted or rehydrated for such usages while remaining undamaged or adversely affected in their cell membrane proteinacious configuration or morphology. The method is believed capable of lyophilization of all cells in mammalian physiological fluids and tissues. Some standard preparation procedures are employed, such as the collecting of the desired number of cells to be processed from whole blood or from cultured cell lines, or tissue as dictated by the assay to be conducted, for an average assay run and reducing them to a pellet form by centrifugation. Initially, this pellet is suspended in a phosphate buffered albumin for a period of time and treated to retrieve the cells in pellet form. Prior to lyophilization, the cell pellet is suspended in a solution of trehalose in an isotonic fluid prepared at a specified optimal concentration and incubated at room temperature for a designated period of time. This suspension treatment of the cells with a designated percent trehalose prepared in an isotonic fluid is repeated at room temperature for the designated time period and the cell suspension is then placed in vials, frozen and lyophilized for a designated period of time.

The lyophilized cells thus produced can be reconstituted with a quantity of distilled water equal to that of the full volume of the vial preparatory to its use in-situ. The reconstituted cells retain their optimal physiological characteristics suitable for use as an analytical control.

BRIEF DESCRIPTION OF THE DRAWINGS

FIG. 5 is a diagrammatic presentation of the lyophilization method steps of the invention for producing lyophilized control cells, cell lines and peripheral blood lymphocytes.

PREFERRED EMBODIMENTS OF THE INVENTION

Figure 1A:
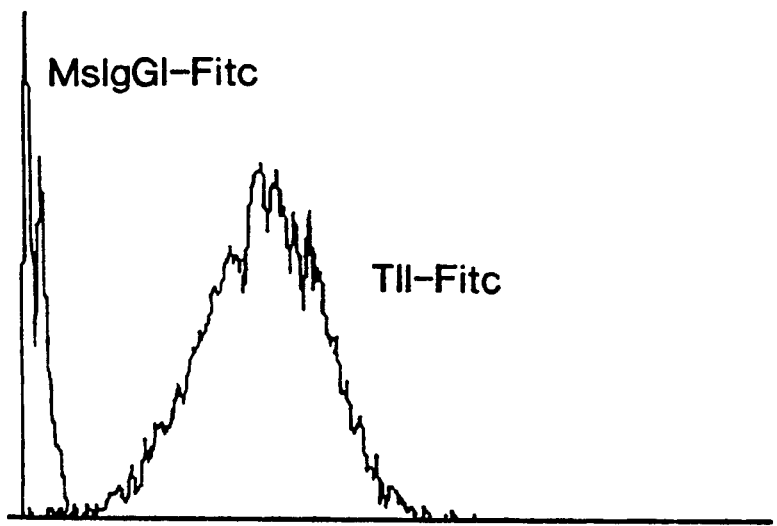
FIG. 1a and FIG. 1b are low cytometer histograms comparing an identical fresh T-cell line (1a) and a T-cell line lyophilized according to the method of this invention (1b) stained with T11-FITC and MsIgG1-FITC labels.

Certain terminology will be employed to explain the results of the comparison tests represented by the histograms depicted in FIGS. 1 through 4. These terms as used herein are defined as follows:

1. "background fluorescence" will refer to the fluorescent glow emanating from any material in a sample other than the specific fluorescent cell under study.

2. "autofluorescence" is one type of background fluorescence wherein the fluorescent glow emanating from a cell is induced by other than a fluorescent chemical, such as a dye.

3. "non-specific binding" will refer to the phenomenon of a fluorescent chemical adhering to a cell surface by means other than the specific method used for effecting its binding to a cell.

4. "light scatter" will refer to the phenomenon occurring in a flow cytometer instrument when an incident beam, such as from a laser source, impinges against a cell and some of the beam is reflected in a multitude of directions and some traverses through the cell. The light scattered, including its angle of reflection and the fluorescence engendered by reason of the fluorescent chemical coated on a cell can be detected and measured for determining cell characteristics such as cell size or volume, cell surface smoothness and number of granules and other structures in the cytoplasm of a cell. Those characteristics are comparable with those of a normal cell.

5. "Mean Channel (MC)" means the average relative amount of fluorescence for the cells analyzed.

6. "Percent positive" means the percentage of analyzed cells which fluoresce more than the background fluorescence.

A list of the ingredients employed in practicing the lyophilization methodology embodying the invention follows:

A. Phosphate buffered albumin solution (PBA) comprising 1 gram PBA in 100 ml of phosphate buffered saline (PBS).

B. Trehalose solution comprising 10 grams of trehalose in 100 ml of an isotonic solution. The preferred isotonic solution was available from Coulter Electronics, Inc. under the registered trademark Isoton® and characterized as absolute.

C. The label "FITC" refers to fluorescein isothiocyanate.

D. The label "RD1" refers to a phycobiliprotein fluorescent marker used by Coulter Corporation.

Refering to FIG. 5, the methodology for practicing the inventive method is described generally. The mammalian cells corresponding to the subject cells to be assayed are collected either from whole blood or from cultured cell lines, or tissue, as dictated by the assay. For an average assay run, $30 \times 10^6$ cells are collected and suspended in a 1% PBS solution at 4 to 8 degrees Centigrade. The suspended cells are centrifuged at 1500 RPM for approximately 10 minutes at room temperature. The supernatant is decanted and the cell pellet is suspended in a 10% trehalose solution prepared in an isotonic fluid such as ISOTON® and incubated at room temperature for ten minutes. The suspension then is centrifuged at 1500 RPM for ten minutes at 4°–8° C. and the resulting pellet is again suspended in a 10% trehalose solution prepared in ISOTON®, for instance, at 4°–8° C. The trehalose treated cell suspension is placed in lyophilization vials at 300 μl of solution per vial, the vials are capped and chilled to 4° C. and then, agitated to assure even and smooth dispersion of cells before being placed in a freezer at −70° C. for at least one (1) hour. Upon expiration of the one (1) hour in the freezer, the vials are placed immediately into a lyophilizer for a period of approximately fifteen (15) hours.

The lyophilized vials are removed from the lyophilizer after expiration of the fifteen (15) hour cycle and stored at between 2°–8° C. For reconstituting, the vial is filled to its 300 μl volume using distilled or deionized water. For conducting a control cell assay on a flow cytometer, the resuspended cells are stained and thereafter analyzed by standard flow cytometer procedures. Of course, such control cells can be used in other types of assays or other suitable diagnostic protocols.

Figure 1B:
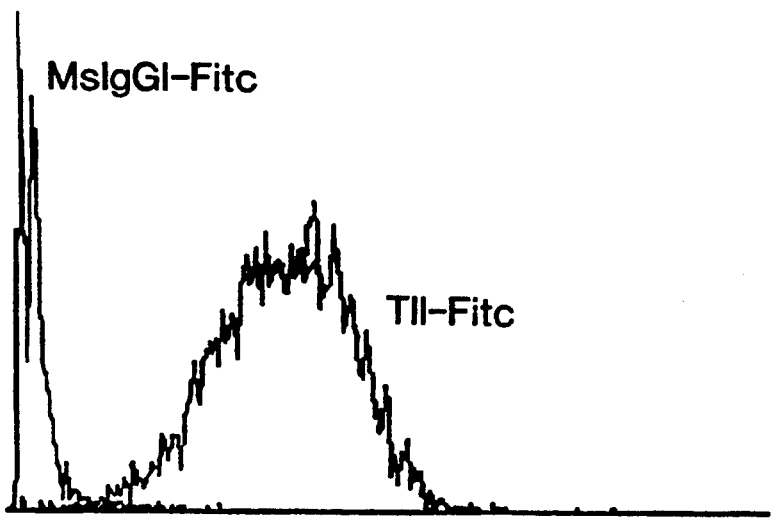

The effectiveness and efficacy of the lyophilized cells produced by the method embodying the invention will become apparent from the detailed discussion with reference to the flow cytometer histograms of the drawing FIGS. 1 through 4 which follows:

Illustrated in FIGS. 1a and 1b flow cytometer histograms in which identical fresh (1a) and lyophilized (1b) T-cell lines identified as PB 44 were stained and compared in an EPICS® flow cytometer marketed by Coulter Corporation of Hialeah, Fla. Two separate lots of PB 44 T-cells were prepared two weeks apart and were lyophilized in accordance with the methodology embodying this invention. The cells were reconstituted or rehydrated using deionized water and stained with cell surface markers using the stained monoclonal antibody MsIgG1-FITC and the stained monoclonal antibody T11-FITC available from Coulter Corporation under the registered trademark COULTER CLONE ®. The procedure for direct immunofluorescence cell surface staining employed is described in detail in a "Coulter Procedures Book", page 4 available from Coulter Corporation and already distributed. After staining, these reconstituted lyophilized cells were analyzed in the EPICS ® flow cytometer to determine percent positivity and relative amount of mean channel fluorescence for each antibody. Fresh cultured PB 44 T-cells obtained on the same day as the assay was conducted were assayed and analyzed similarly for comparison of results with those of the assayed stained lyophilized cells. The histogram results are as follows:

|  | PB 44 T-CELLS | | | |
|---|---|---|---|---|
|  | Fresh Cells | | Lyophilized Cells | |
|  | MC | % Positive | MC | % Positive |
| T11-FITC | 84 | 99 | 92 | 100 |
| MsIgG1-FITC | — | 0 | 16 | 5 |

The percent reactivity on the lyophilized T-cells was equivalent to that of the fresh T-cells analyzed. The mean cell fluorescence in each instance also was substantially equivalent, the slight discrepancy of 84 to 92 being insufficient to interfere with acceptable assay results. The obvious similarity between the histogram of FIG. 1a for fresh T-cells and the histogram of FIG. 1b for lyophilized T-cells is to be noted. The lyophilization method embodying the invention clearly provides for the desirable advantages attributed to this invention.

Additional assays on the EPICS ® flow cytometer using a series of COULTER CLONE ® monoclonal antibodies with fresh and lyophilized T-cells of the PB 44 cell line were conducted. The procedure for preparation of the stained cells used was the same as previously described. The results of the additional assays were as follows:

|  | PB 44 T-Cell Results | | | |
|---|---|---|---|---|
|  | Fresh PB 44 | | Lyophilized PB 44 | |
| Coulter Clone ® Antibody | Experiment # | MC* | Percent Positive | MC | Percent Positive |
| IgG1-FITC | 1 | 10 | 0 | 19 | 13 |
| (Isotype Control) | 2 | 12 | 0 | 16 | 5 |
| IgG1-RD1 | 1 | 3 | 0 | 4 | 1 |
| (Isotype Control) | 2 | 6 | 0 | 5 | 0 |
| T11-FITC | 1 | 84 | 100 | 86 | 99 |
|  | 2 | 103 | 100 | 108 | 99 |
| T8-FITC | 1 | 86 | 97 | 96 | 98 |
|  | 2 | 113 | 100 | 116 | 100 |
| T4-FITC | 1 | 40 | 71 | 50 | 84 |
|  | 2 | 69 | 93 | 67 | 95 |
| 4B4-FITC | 1 | 40 | 79 | 51 | 92 |
|  | 2 | 75 | 100 | 70 | 99 |
| T11-RD1 | 1 | 98 | 100 | 77 | 95 |
|  | 2 | 120 | 100 | 105 | 100 |
| T8-RD1 | 1 | 110 | 91 | 109 | 98 |
|  | 2 | 141 | 100 | 126 | 99 |

Percent reactivity on lyophilized PB 44 cells was substantially equivalent to that of fresh cells for each of the antibodies tested. In addition, mean channel values which give a measure of relative fluorescence intensity of the stained cells, were similar for lyophilized versus fresh cells. In some cases, lyophilized cells did exhibit a greater degree of non-specific fluorescence as judged by staining with the IgG1-FITC Isotype control. This degree of fluorescence, because of its low intensity, however, is considered insufficient to interfere with acceptable assay interpretations.

Figure 2A:
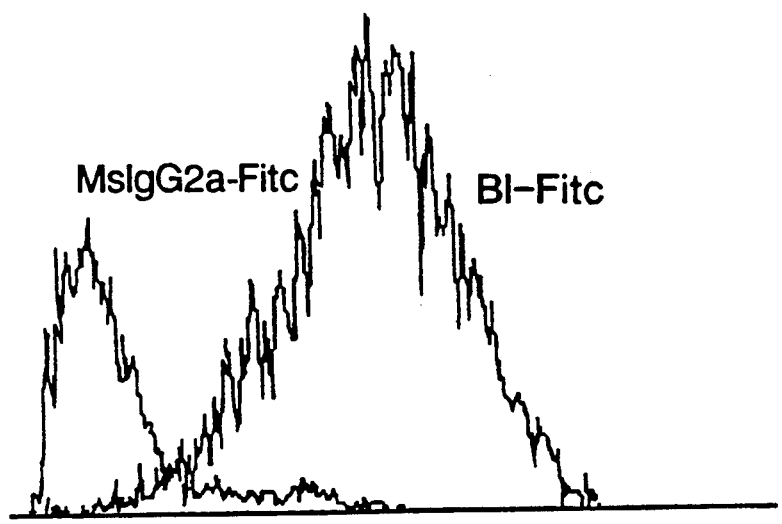
FIG. 2a and FIG. 2b are flow cytometer histograms comparing an identical B-cell line lyophilized according to the method embodying the invention (2b) and a fresh B-cell line (1a) stained with B1-FITC and MsIgG2a-FITC labels.
Figure 2B:
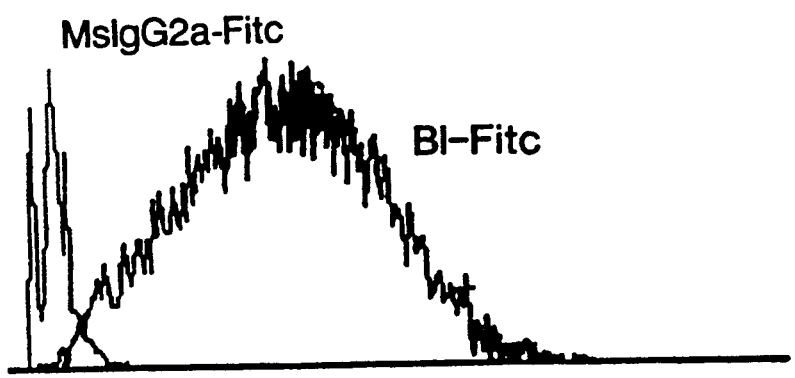
Figure 3C:
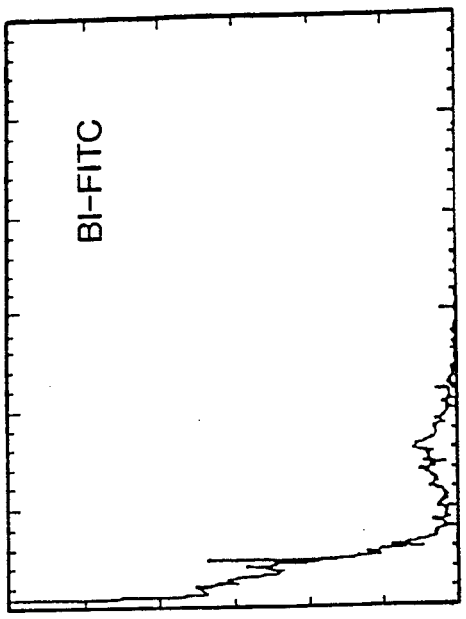
FIGS. 3a–3d are four flow cytometer histograms comparing fresh (3a and 3b) and lyophilized (3c and 3d) peripheral blood lymphocytes using dual color stained T11 and B1 monoclonal antibodies.
Figure 3D:
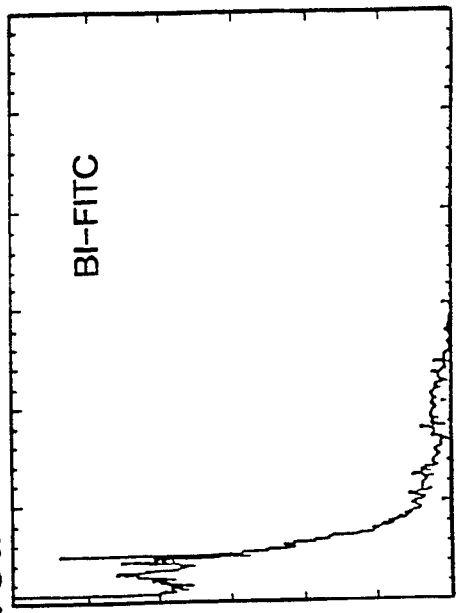
Figure 3A:
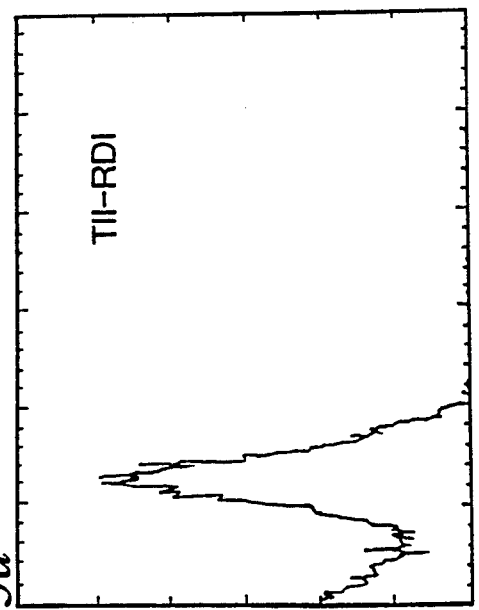
Figure 3B:
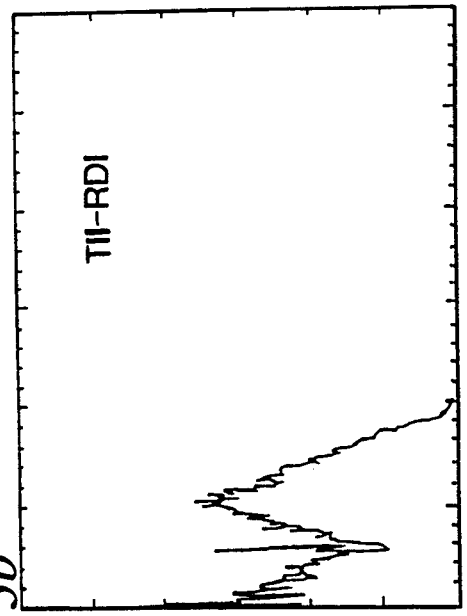
Figure 4C:
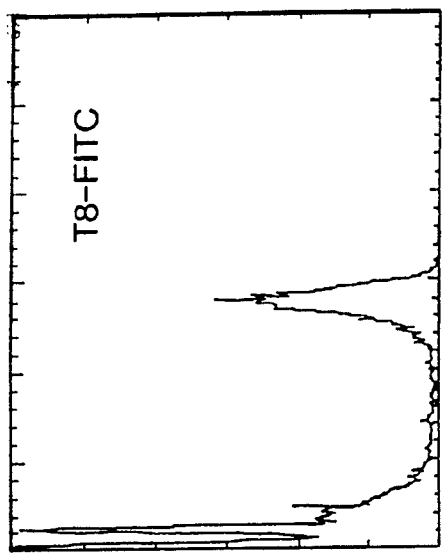
FIGS. 4a–4d are four flow cytometer histograms comparing fresh (4a–4b) and lyophilized (4c and 4d) peripheral blood lymphocytes using dual color stained T4 and T8 monoclonal antibodies.
Figure 4D:
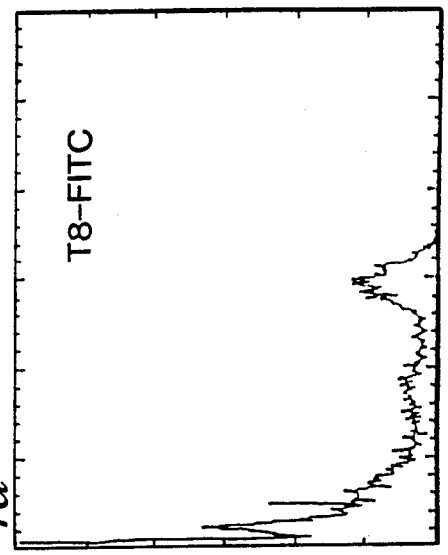
Figure 4A:
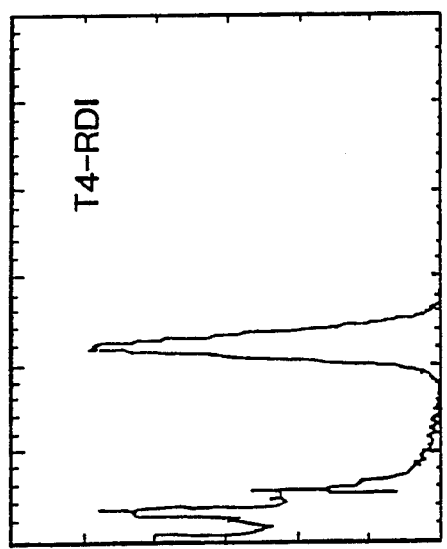
Figure 4B:
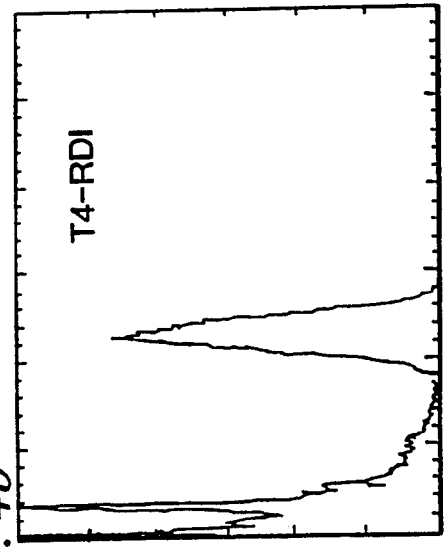

Illustrated in FIGS. 2a and 2b flow cytometric histograms in which an identical fresh (2a) and lyophilized (2b) B-cell line identified as PB 11 were stained and compared in an EPICS ® flow cytometer using B1-FITC. Two separate lots of PB 11 B-cells prepared two weeks apart were lyophilized in accordance with the invention. The cells were rehydrated using deionized water and stained with B1-FITC and B4-FITC cell markers also available from Coulter Corporation under the trademark "COULTER CLONE". The staining procedure was the same as described with respect to FIGS. 1a and 1b. After staining, the rehydrated lyophilized cells were analyzed in the EPICS ® instrument to determine percent positivity and relative amount of mean channel fluorescence for each antibody. Fresh PB 11 B-cells, obtained from culture vessels on the same day as the assay was conducted, were assayed and analyzed similarly for comparison of data with those of assayed stained lyophilized cells. The results of the B1-FITC and B4-FITC data are as follows:

|  | PB 11 B-Cells | | | |
|---|---|---|---|---|
|  | Fresh Cells | | Lyophilized Cells | |
|  | MC | % Positive | MC | % Positive |
| B1-FITC | 82 | 99 | 118 | 100 |
| B4-FITC | 92 | 100 | 69 | 99 |
|  | 70 | 99 | 71 | 99 |

The percent reactivity and mean channel fluorescence on lyophilized B-cells was equivalent to that of fresh cells. Lyophilized cells did exhibit a greater degree of non-specific fluorescence in the isotype control, but this is attributed to non-specific background staining observed with this cell line on a day-to-day basis. This degree of non-specific fluorescence, because of its low intensity, does not interfere with assay interpretations.

Referring to FIGS. 3a–3d, the four flow cytometer histograms compare fresh (3a and 3b) and lyophilized (3c and 3d) peripheral blood lymphocytes (PBLS) using dual color T11 and B1 COULTER CLONE ® monoclonal antibodies. The cells were separated by Ficoll-Hypaque ® standard methodology. Lyophilization and staining of cells were in accordance with such procedures previously described and the cells analyzed. The concluded results were as follows:

|  | Fresh Cells | | Lyophilized Cells | |
|---|---|---|---|---|
|  | MC | % Positive | MC | % Positive |
| B1-FITC | 70 | 12 | 59 | 19 |
| T11-RD1 | 64 | 77 | 57 | 67 |

Percent reactivity on lyophilized preparations of peripheral blood lymphocytes was substantially equivalent to that of fresh PBLS for each antibody tested. Mean channel fluorescence also was substantially equivalent.

Referring to FIGS. 4a–4d, the four flow cytometer histograms compare fresh (4a and 4b) and lyophilized (4c and 4d) peripheral blood lymphocytes (PBLS) using dual color stained T4 and T8 COULTER CLONE ® monoclonal antibodies. The same preparatory procedures as described for FIGS. 3a–3d were used for these assays. The concluded results were as follows:

|  | Fresh Cells | | Lyophilized Cells | |
| --- | --- | --- | --- | --- |
|  | MC | % Positive | MC | % Positive |
| T4RD1 | 102 | 47 | 105 | 58 |
| T8-FITC | 119 | 31 | 99 | 32 |

The percent reactivity of lyophilized PBLS was substantially equivalent to that of fresh PBLS for each of the monoclonal antibodies tested. Mean Channel fluorescence also was substantially equivalent for both types of PBLS, although the T8 stained monoclonal antibody on the lyophilized PBLS was slightly depressed, but this did not interfere with overall analyses or comparison.

Shelf life tests were conducted in which the lyophilized mammalian cells were stored in a refrigerator at between 2°–8° C. The results derived from this exercise indicate real time stability of lyophilized product in excess of five (5) months.

Two stabilized preparations of human T and B cells lyophilized in accordance with the invention were tested in the EPICS ® flow cytometer to ascertain the extent of their structural preservation as compared to fresh human T and B cell preparations. One mixture consisted of 80% T cells and 20% B cells and the second mixture consisted of 50% each of T and B cells. The lyophilized cells were reconstituted with distilled water and their light scatter patterns on the flow cytometer were charted, i.e., forward angle light scatter (FALS) and 90 light scatter. The same light scatter test patterns were charted for corresponding preparations of fresh T and B cells in the EPICS ® flow cytometer. The charted test results established that the light scatter patterns of the lyophilized cell mixtures were similar to those of corresponding fresh cell mixtures so as to indicate excellent structural preservation of the lyophilized cells.

The tests also indicated that the cell surface antigenicity of the cells was not impaired. COULTER CLONE ® monoclonal antibodies, suitably stained, were utilized which included T4, T8, T11, B1, B4, I2 and 4B4 monoclonals.

A series of tests were conducted in which lyophilized cells were positively stained and tested in an EPICS ® flow cytometer as biological controls for DNA analysis. Fresh and lyophilized cells were stained and tested to analyze for cell cycle development in the fresh and lyophilized cell populations.

Fresh and lyophilized cells were obtained on different days and from different donors (designated PBL's) and different cultures designated PB11 and PB44 were obtained. The charted results of those tests corroborated the suitability of the lyophilized cells for use as control cells for cell cycle analysis. Some deviations in cell cycle analyses between fresh and lyophilized cell comparisons could be attributed to differences in time periods of obtainment of the cells tested.

From the foregoing comparison analyses between cells lyophilized according to the invention and corresponding fresh cells the following conclusions can be derived:

1. These lyophilized cells can be used for in vitro diagnostic analyses in quality control of flow cytometry procedures.

2. These lyophilized cells can function as positively stained biological controls for cell surface marker analysis by flow cytometer instrumentation. In these functions they can be used to assess reagent integrity, sample preparation technique, and proper flow cytometer function. They can serve as cell controls for specialized panels of monoclonal antibodies against cellular activation antigens and leukemia antigens. They can serve as standards in quantifying antigen density on cell surfaces.

3. These lyophilized cells can function as positively stained biological controls for DNA analysis to assess reagent integrity, sample preparation technique, and proper flow cytometer function. Also, they can serve as standards for cell cycle analysis of cell populations.

It is believed that the retained morphology and cell surface antigenicity of these lyophilized cells would enable their use also as control cells in other types of assays, such as of the ELISA and microscopy type. It is believed that the cells prepared by the lyophilizing method of the invention can be employed for immunoassay of all normal or abnormal mammalian cells, such as cancer cells. This is feasible so long as the assay medium, such as a monoclonal antibody, is available for detection purposes to complete the assay. The lyophilization method embodying the invention also could produce lyophilized control cells suitable for use with hematology particle analyzers as well. Tissue cells also could be preserved by the inventive method.

The enumerated advantages to be derived from using these lyophilized control cells in flow cytometry as compared to the current practice of using fluorescent beads or microspheres can be appreciated. Fluorescent microspheres are not suitable for use as a control for sample preparation, are not useful for selecting proper flow cytometer settings for light scatter analyses of cells and their fluorescence is intracellular and not cell surface. Further, the lyophilized cells are more structurally similar to fresh cells analyzed by flow cytometric procedures.

It further is noted that preserved cells lyophilized by this invention do not require the absolute storage conditions or complex handling procedures for rehydration which are encountered for normal peripheral blood cells (PBL's) preserved by using cryoprotectorants and stored at liquid nitrogen temperatures.

It is contemplated that minor variations in practicing the method of the invention, such as incubation period or reagent quantity, may occur to persons skilled in the art without departing from the spirit of the invention as defined in the appended claims.

We claim:

1. Lyophilized mammalian cells which have been lyophilized by means including isotonic trehalose solutions so as to be capable of being rehydrated in water to exhibit structural and cell surface antigenicity characteristics which authentically simulate the structural and cell surface antigenicity characteristics of the corresponding fresh cells prior to lyophilization so that said lyophilized cells can function effectively as biological control cells in immunological analysis procedures, said structural features capable of being authenticated by flow cytometric light scatter analysis and said cell antigenicity characteristics capable of authentication by flow cytometer fluorescence analysis, said lyophilized cells capable of exhibiting a real time stability after preservation at between 2 to 8 degrees Centigrade for at least approximately a five month period of time.

2. The lyophilized cells as described in claim 1 wherein said rehydrated are cells capable of being used as biological control cells in flow cytometry methodologies for DNA analysis, cell cycle analysis of cell populations and immunology.

3. Lyophilized cells in accordance with claim 1 wherein said cells are suitable for replacing fresh cells as standards in cell flow cytometer cell cycle analyses of T and B cell populations.

4. The lyophilized cells as described in claim 1 in which said cells are derived from mammalian tissue cells which are normal in their physiological state.

5. The lyophilized cells as described in claim 1, in which said cells are derived from mammalian peripheral blood cells or cultured cells.

6. The lyophilized cells as described in claim 1 in which said cells are derived from mammalian tissue cells which are abnormal in their physiological state.

7. Lyophilized mammalian cells prepared in an isotonic trehalose solution, wherein said lyophilized cells are capable of being reconstituted in distilled water after storage at refrigeration temperatures at between 2 to 8 degrees Centigrade for a minimum period of time of approximately five months, said cells retaining their original membrane structure and cell surface antigenicity characteristics, whereby said reconstituted cells are suitable for subsequent use as positive immunologically stained biological control cells, replacing positive immunologically stained fresh cells, in a flow cytometer.

8. The lyophilized cells as described in claim 7, wherein said cells, when reconstituted, are viable for use as biological control cells in DNA analytical methods in a flow cytometer.

9. The lyophilized cells as described in claim 7, wherein said cells, when reconstituted, are viable for use as standards in flow cytometer cell cycle analyses of T and B cell populations.

10. A process for preparing lyophilized mammalian cells wherein said cells retain their cell membrane structure integrity and cell surface antigenicity characteristics when reconstituted, said process comprising the steps of:
   A. collecting a sample having a predetermined number or cells suspended in a selected volume of phosphate buffered albumin;
   B. subjecting the cell suspension to centrifugation to obtain a cell pellet;
   C. incubating the cell pellet in a solution of trehalose in an isotonic fluid for a predetermined time period at ambient room temperature to obtain a cell suspension;
   D. introducing the cell suspension to a vessel, chilling to a prescribed reduced temperature and freezing at about $-70°$ C. for approximately one hour;
   E. removing the vessel to a lyophilizer apparatus for a prescribed lyophilizing cycle; and
   F. storing at refrigeration temperatures of between 2–8 degrees Centigrade for subsequent reconstitution in distilled water in situ.

11. The process as described in claim 10 wherein the cell suspension derived from step C is again subjected to steps B and C before subjecting the resulting cell suspension to step D.

12. The process as described in claim 10 or 11 in which the incubation is performed in 10% trehalose in isotonic solution.

13. The process as described in claim 12 in which the cell pellet is incubated in the 10% trehalose isotonic solution for approximately thirty minutes at ambient room temperature.

14. The process as described in claim 10 or 11 in which the cell pellet is suspended in phosphate buffered albumin for one hour at 4° C.

15. The process as described in claim 10 or 11 in which the lyophilizing cycle is approximately fifteen hours.

16. In an assay of mammalian physiological cells wherein a control sample of physiological cells is analyzed by standard techniques for the purpose of standardizing the assay reagents and instrumentation, and said control cells are fresh mammalian physiological cells, wherein the improvement comprises replacing said fresh control cells with lyophilized mammalian cells prepared by an isotonic trehalose solution, which lyophilized cells are capable of reconstitution in water, said reconstituted lyophilized cells retaining the cell membrane structure integrity and cell surface antigenicity characteristics of corresponding fresh mammalian cells.

17. The assay as described in claim 16 in which said mammalian cells are selected from peripheral blood cells, cultured cells, hybridoma cell lines or tissue cells.

18. The assay as described in claim 16 in which the assay is for detecting discrete cell populations of peripheral blood cells.

19. Lyophilized mammalian cells prepared by an isotonic trehalose solution, which cells are capable of being reconstituted in distilled water after storage at refrigeration temperatures for a minimum time of about five months at between 2 to 8 degrees centigrade, said cells retaining substantially equivalent membrane structural and cell surface antigenicity characteristics as compared to fresh cells.

20. The lyophilized cells as described in claim 19, wherein said cells, when reconstituted, retain the membrane structural characteristics and cell surface antigenicity characteristics of the corresponding fresh cells, which retention thereby enables them to serve as replacements for fresh mammalian control cells in mammalian cell analytical methods selected from the group consisting of flow cytometry, immunological assays, blood cell counting, and sizing and analysis of subsets of blood cell constituents.

* * * * *